(12) United States Patent
Kim et al.

(10) Patent No.: US 10,508,138 B2
(45) Date of Patent: Dec. 17, 2019

(54) POLYPEPTIDE CAPABLE OF BINDING TO VASCULAR ENDOTHELIAL GROWTH FACTOR, AND USE THEREOF

(71) Applicant: Korea Advanced Institute of Science and Technology, Daejeon (KR)

(72) Inventors: Hak-Sung Kim, Daejeon (KR); Da Eun Hwang, Daejeon (KR); Jeong Hyun Ryou, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 15/737,937

(22) PCT Filed: Sep. 16, 2015

(86) PCT No.: PCT/KR2015/009710
§ 371 (c)(1),
(2) Date: Dec. 19, 2017

(87) PCT Pub. No.: WO2016/204341
PCT Pub. Date: Dec. 22, 2016

(65) Prior Publication Data
US 2018/0170980 A1    Jun. 21, 2018

(30) Foreign Application Priority Data
Jun. 19, 2015  (KR) .......................... 10-2015-0087476

(51) Int. Cl.
| | |
|---|---|
| C07K 14/00 | (2006.01) |
| C07K 14/475 | (2006.01) |
| A61K 38/16 | (2006.01) |
| C07K 14/46 | (2006.01) |
| A61P 27/02 | (2006.01) |
| A61P 35/00 | (2006.01) |
| A61K 38/00 | (2006.01) |

(52) U.S. Cl.
CPC ............ *C07K 14/461* (2013.01); *A61P 27/02* (2018.01); *A61P 35/00* (2018.01); *A61K 38/00* (2013.01); *C07K 2319/70* (2013.01)

(58) Field of Classification Search
None
See application file for complete search history.

(56) References Cited

U.S. PATENT DOCUMENTS

2009/0082274 A1    3/2009    Stumpp et al.

FOREIGN PATENT DOCUMENTS

| KR | 10-2011-0099600 A | 9/2011 |
|---|---|---|
| KR | 10-1356075 B1 | 2/2014 |
| KR | 10-2014-0094837 A | 7/2014 |
| KR | 10-1517196 B1 | 5/2015 |
| KR | 101654890 B1 | 8/2016 |

OTHER PUBLICATIONS

Fan, H., et al, "Decorin derived antiangiogenic peptide LRR5 inhibits endothelial cell migration by interfering with VEGF-stimulated NO release", "The International Journal of Biochemistry & Cell Biology", Feb. 17, 2008, pp. 2120-2128, vol. 40.

*Primary Examiner* — Christine J Saoud
*Assistant Examiner* — Jon M Lockard
(74) *Attorney, Agent, or Firm* — Hultquist, PLLC; Steven J. Hultquist (57) ABSTRACT

The present disclosure relates to a novel polypeptide capable of binding specifically to vascular endothelial growth factor, a polynucleotide encoding the polypeptide, a vector comprising the polynucleotide, a recombinant microorganism including the expression vector, a method of producing the polypeptide using the recombinant microorganism, a composition for treating or preventing age-related macular degeneration or cancer, which comprises the polypeptide, and a method for preventing or treating age-related macular degeneration or cancer, which comprises administering the composition for treating or preventing age-related macular degeneration or cancer, which comprises the polypeptide. The disclosed polypeptide is capable of binding to vascular endothelial growth factor to inhibit the activity thereof, and thus can be widely used as an agent for treating and preventing various diseases associated with vascular endothelial growth factor (VEGF).

3 Claims, 4 Drawing Sheets
(3 of 4 Drawing Sheet(s) Filed in Color)
Specification includes a Sequence Listing.

SEQUENCE LISTING

```
<160> NUMBER OF SEQ ID NOS: 10

<210> SEQ ID NO 1
<211> LENGTH: 798
<212> TYPE: DNA
<213> ORGANISM: Artificial Sequence
<220> FEATURE:
<223> OTHER INFORMATION: Repebody-Library
<220> FEATURE:
<221> NAME/KEY: misc_feature
<222> LOCATION: (139)..(140)
<223> OTHER INFORMATION: n is a, c, g, or t
<220> FEATURE:
<221> NAME/KEY: misc_feature
<222> LOCATION: (145)..(146)
<223> OTHER INFORMATION: n is a, c, g, or t
<220> FEATURE:
<221> NAME/KEY: misc_feature
<222> LOCATION: (148)..(149)
<223> OTHER INFORMATION: n is a, c, g, or t
<220> FEATURE:
<221> NAME/KEY: misc_feature
<222> LOCATION: (205)..(206)
<223> OTHER INFORMATION: n is a, c, g, or t
<220> FEATURE:
<221> NAME/KEY: misc_feature
<222> LOCATION: (211)..(212)
<223> OTHER INFORMATION: n is a, c, g, or t
<220> FEATURE:
<221> NAME/KEY: misc_feature
<222> LOCATION: (214)..(215)
<223> OTHER INFORMATION: n is a, c, g, or t
```

<400> SEQUENCE: 1

```
gaaaccatta ccgtgagcac cccgatcaaa cagattttc cggatgacgc gttcgccgaa      60
acgatcaaag caaacctgaa gaaaagagc gttaccgatg ctgtcacgca aaatgaactg     120
aacagtattg accagatcnn kgcgnnknnk tccgatatca aatcagtgca aggcattcag    180
tatctgccga atgttcgtta cctgnnkctg nnknnkaaca aactgcatga catctcggca    240
ctgaaagaac tgaccaatct gacgtatctg attctgaccg gtaaccaact gcagagcctg    300
ccgaatggcg tctttgataa actgacgaac ctgaaagaac tggtgctggt tgaaaatcaa    360
ctgcagtctc tgccggacgg tgtcttcgat aaactgacca acctgacgta cctgaatctg    420
gctcacaacc aactgcagag tctgccgaaa ggcgtgtttg acaaactgac caatctgacg    480
gaactggatc tgtcctataa ccaactgcag tcactgccgg aaggtgtttt cgacaaactg    540
acccagctga agatctgcg cctgtaccag aatcagctga atcggtccc ggacggcgtg     600
tttgatcgtc tgaccagcct gcagtatatc tggctgcatg ataacccgtg ggattgcacc    660
tgtccgggta ttcgctacct gtctgaatgg atcaataaac acagtggcgt tgtccgtaac    720
tccgcgggtt cagttgcccc ggattcggcg aaatgctccg cagcggtaa accggtgcgt     780
agcattattt gcccgacc                                                  798
```

<210> SEQ ID NO 2
<211> LENGTH: 266
<212> TYPE: PRT
<213> ORGANISM: Artificial Sequence
<220> FEATURE:
<223> OTHER INFORMATION: Repebody-Library_Protein
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(72)
<223> OTHER INFORMATION: Xaa can be any naturally occurring amino acid

<400> SEQUENCE: 2

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Xaa Ala
        35                  40                  45

Xaa Xaa Ser Asp Ile Lys Ser Val Gln Gly Ile Gln Tyr Leu Pro Asn
    50                  55                  60

Val Arg Tyr Leu Xaa Leu Xaa Xaa Asn Lys Leu His Asp Ile Ser Ala
65                  70                  75                  80

Leu Lys Glu Leu Thr Asn Leu Thr Tyr Leu Ile Leu Thr Gly Asn Gln
                85                  90                  95

Leu Gln Ser Leu Pro Asn Gly Val Phe Asp Lys Leu Thr Asn Leu Lys
            100                 105                 110

Glu Leu Val Leu Val Glu Asn Gln Leu Gln Ser Leu Pro Asp Gly Val
        115                 120                 125
```

-continued

Phe Asp Lys Leu Thr Asn Leu Thr Tyr Leu Asn Leu Ala His Asn Gln
        130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
        180                 185                 190

Leu Lys Ser Val Pro Asp Gly Val Phe Asp Arg Leu Thr Ser Leu Gln
                195                 200                 205

Tyr Ile Trp Leu His Asp Asn Pro Trp Asp Cys Thr Cys Pro Gly Ile
        210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
        260                 265

<210> SEQ ID NO 3
<211> LENGTH: 266
<212> TYPE: PRT
<213> ORGANISM: Artificial Sequence
<220> FEATURE:
<223> OTHER INFORMATION: Repebody-A1

<400> SEQUENCE: 3

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Val Ala
            35                  40                  45

Tyr Arg Ser Asp Ile Lys Ser Val Gln Gly Ile Gln Tyr Leu Pro Asn
        50                  55                  60

Val Arg Tyr Leu Val Leu Leu Gln Asn Lys Leu His Asp Ile Ser Ala
65                  70                  75                  80

Leu Lys Glu Leu Thr Asn Leu Thr Tyr Leu Ile Leu Thr Gly Asn Gln
                85                  90                  95

Leu Gln Ser Leu Pro Asn Gly Val Phe Asp Lys Leu Thr Asn Leu Lys
            100                 105                 110

Glu Leu Val Leu Val Glu Asn Gln Leu Gln Ser Leu Pro Asp Gly Val
        115                 120                 125

Phe Asp Lys Leu Thr Asn Leu Thr Tyr Leu Asn Leu Ala His Asn Gln
        130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
        180                 185                 190

Leu Lys Ser Val Pro Asp Gly Val Phe Asp Arg Leu Thr Ser Leu Gln
                195                 200                 205

Tyr Ile Trp Leu His Asp Asn Pro Trp Asp Cys Thr Cys Pro Gly Ile
        210                 215                 220

```
Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
            245                 250                 255

Lys Pro Val Arg Ser Ile Ile Cys Pro Thr
            260                 265
```

<210> SEQ ID NO 4
<211> LENGTH: 266
<212> TYPE: PRT
<213> ORGANISM: Artificial Sequence
<220> FEATURE:
<223> OTHER INFORMATION: Repebody-C2

<400> SEQUENCE: 4

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
            35                  40                  45

Tyr Gln Ser Asp Ile Lys Ser Val Gln Gly Ile Gln Tyr Leu Pro Asn
50                  55                  60

Val Arg Tyr Leu Ile Leu Leu Gln Asn Lys Leu His Asp Ile Ser Ala
65                  70                  75                  80

Leu Lys Glu Leu Thr Asn Leu Thr Tyr Leu Ile Leu Thr Gly Asn Gln
                85                  90                  95

Leu Gln Ser Leu Pro Asn Gly Val Phe Asp Lys Leu Thr Asn Leu Lys
            100                 105                 110

Glu Leu Val Leu Val Glu Asn Gln Leu Gln Ser Leu Pro Asp Gly Val
            115                 120                 125

Phe Asp Lys Leu Thr Asn Leu Thr Tyr Leu Asn Leu Ala His Asn Gln
130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
            195                 200                 205

Tyr Ile Trp Leu His Asp Asn Pro Trp Asp Cys Thr Cys Pro Gly Ile
210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
            245                 250                 255

Lys Pro Val Arg Ser Ile Ile Cys Pro Thr
            260                 265
```

<210> SEQ ID NO 5
<211> LENGTH: 266
<212> TYPE: PRT
<213> ORGANISM: Artificial Sequence
<220> FEATURE:
<223> OTHER INFORMATION: Repebody-C3

<400> SEQUENCE: 5

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Val Ala
        35                  40                  45

Met Gln Ser Asp Ile Lys Ser Val Gln Gly Ile Gln Tyr Leu Pro Asn
    50                  55                  60

Val Arg Tyr Leu Val Leu Ile Gln Asn Lys Leu His Asp Ile Ser Ala
65                  70                  75                  80

Leu Lys Glu Leu Thr Asn Leu Thr Tyr Leu Ile Leu Thr Gly Asn Gln
                85                  90                  95

Leu Gln Ser Leu Pro Asn Gly Val Phe Asp Lys Leu Thr Asn Leu Lys
            100                 105                 110

Glu Leu Val Leu Val Glu Asn Gln Leu Gln Ser Leu Pro Asp Gly Val
            115                 120                 125

Phe Asp Lys Leu Thr Asn Leu Thr Tyr Leu Asn Leu Ala His Asn Gln
        130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
            195                 200                 205

Tyr Ile Trp Leu His Asp Asn Pro Trp Asp Cys Thr Cys Pro Gly Ile
        210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
            245                 250                 255

Lys Pro Val Arg Ser Ile Ile Cys Pro Thr
            260                 265

<210> SEQ ID NO 6
<211> LENGTH: 266
<212> TYPE: PRT
<213> ORGANISM: Artificial Sequence
<220> FEATURE:
<223> OTHER INFORMATION: Repebody-E4

<400> SEQUENCE: 6

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Leu Ala
        35                  40                  45

Tyr Gln Ser Asp Ile Lys Ser Val Gln Gly Ile Gln Tyr Leu Pro Asn
    50                  55                  60

Val Arg Tyr Leu Ile Leu Leu Val Asn Lys Leu His Asp Ile Ser Ala
65                  70                  75                  80

Leu Lys Glu Leu Thr Asn Leu Thr Tyr Leu Ile Leu Thr Gly Asn Gln
                85                  90                  95

Leu Gln Ser Leu Pro Asn Gly Val Phe Asp Lys Leu Thr Asn Leu Lys
            100                 105                 110

Glu Leu Val Leu Val Glu Asn Gln Leu Gln Ser Leu Pro Asp Gly Val
        115                 120                 125

Phe Asp Lys Leu Thr Asn Leu Thr Tyr Leu Asn Leu Ala His Asn Gln
    130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 7
<211> LENGTH: 266
<212> TYPE: PRT
<213> ORGANISM: Artificial Sequence
<220> FEATURE:
<223> OTHER INFORMATION: Repebody-E7

<400> SEQUENCE: 7

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Met Ala
        35                  40                  45

Met Gln Ser Asp Ile Lys Ser Val Gln Gly Ile Gln Tyr Leu Pro Asn
    50                  55                  60

Val Arg Tyr Leu Phe Leu Phe Gln Asn Lys Leu His Asp Ile Ser Ala
65                  70                  75                  80

Leu Lys Glu Leu Thr Asn Leu Thr Tyr Leu Ile Leu Thr Gly Asn Gln
                85                  90                  95

Leu Gln Ser Leu Pro Asn Gly Val Phe Asp Lys Leu Thr Asn Leu Lys
            100                 105                 110

Glu Leu Val Leu Val Glu Asn Gln Leu Gln Ser Leu Pro Asp Gly Val
        115                 120                 125

Phe Asp Lys Leu Thr Asn Leu Thr Tyr Leu Asn Leu Ala His Asn Gln
    130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

```
Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 8
<211> LENGTH: 266
<212> TYPE: PRT
<213> ORGANISM: Artificial Sequence
<220> FEATURE:
<223> OTHER INFORMATION: Repebody-F1

<400> SEQUENCE: 8

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Tyr Asn Ser Asp Ile Lys Ser Val Gln Gly Ile Gln Tyr Leu Pro Asn
    50                  55                  60

Val Arg Tyr Leu Ile Leu Ile Arg Asn Lys Leu His Asp Ile Ser Ala
65                  70                  75                  80

Leu Lys Glu Leu Thr Asn Leu Thr Tyr Leu Ile Leu Thr Gly Asn Gln
                85                  90                  95

Leu Gln Ser Leu Pro Asn Gly Val Phe Asp Lys Leu Thr Asn Leu Lys
            100                 105                 110

Glu Leu Val Leu Val Glu Asn Gln Leu Gln Ser Leu Pro Asp Gly Val
        115                 120                 125

Phe Asp Lys Leu Thr Asn Leu Thr Tyr Leu Asn Leu Ala His Asn Gln
    130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265
```

```
<210> SEQ ID NO 9
<211> LENGTH: 266
<212> TYPE: PRT
<213> ORGANISM: Artificial Sequence
<220> FEATURE:
<223> OTHER INFORMATION: Repebody-A1-D44G

<400> SEQUENCE: 9

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Gly Gln Ile Val Ala
        35                  40                  45

Tyr Arg Ser Asp Ile Lys Ser Val Gln Gly Ile Gln Tyr Leu Pro Asn
    50                  55                  60

Val Arg Tyr Leu Val Leu Leu Gln Asn Lys Leu His Asp Ile Ser Ala
65                  70                  75                  80

Leu Lys Glu Leu Thr Asn Leu Thr Tyr Leu Ile Leu Thr Gly Asn Gln
                85                  90                  95

Leu Gln Ser Leu Pro Asn Gly Val Phe Asp Lys Leu Thr Asn Leu Lys
            100                 105                 110

Glu Leu Val Leu Val Glu Asn Gln Leu Gln Ser Leu Pro Asp Gly Val
        115                 120                 125

Phe Asp Lys Leu Thr Asn Leu Thr Tyr Leu Asn Leu Ala His Asn Gln
130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 10
<211> LENGTH: 266
<212> TYPE: PRT
<213> ORGANISM: Artificial Sequence
<220> FEATURE:
<223> OTHER INFORMATION: Repebody-C2-D44G

<400> SEQUENCE: 10

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Gly Gln Ile Ile Ala
        35                  40                  45
```

-continued

```
Tyr Gln Ser Asp Ile Lys Ser Val Gln Gly Ile Gln Tyr Leu Pro Asn
    50                  55                  60
Val Arg Tyr Leu Ile Leu Leu Gln Asn Lys Leu His Asp Ile Ser Ala
65                  70                  75                  80
Leu Lys Glu Leu Thr Asn Leu Thr Tyr Leu Ile Leu Thr Gly Asn Gln
                85                  90                  95
Leu Gln Ser Leu Pro Asn Gly Val Phe Asp Lys Leu Thr Asn Leu Lys
                100                 105                 110
Glu Leu Val Leu Val Glu Asn Gln Leu Gln Ser Leu Pro Asp Gly Val
            115                 120                 125
Phe Asp Lys Leu Thr Asn Leu Thr Tyr Leu Asn Leu Ala His Asn Gln
    130                 135                 140
Leu Gln Ser Leu Pro Lys Gly Val Phe Asp Lys Leu Thr Asn Leu Thr
145                 150                 155                 160
Glu Leu Asp Leu Ser Tyr Asn Gln Leu Gln Ser Leu Pro Glu Gly Val
                165                 170                 175
Phe Asp Lys Leu Thr Gln Leu Lys Asp Leu Arg Leu Tyr Gln Asn Gln
            180                 185                 190
Leu Lys Ser Val Pro Asp Gly Val Phe Asp Arg Leu Thr Ser Leu Gln
            195                 200                 205
Tyr Ile Trp Leu His Asp Asn Pro Trp Asp Cys Thr Cys Pro Gly Ile
            210                 215                 220
Arg Tyr Leu Ser Glu Trp Ile Asn Lys His Ser Gly Val Val Arg Asn
225                 230                 235                 240
Ser Ala Gly Ser Val Ala Pro Asp Ser Ala Lys Cys Ser Gly Ser Gly
                245                 250                 255
Lys Pro Val Arg Ser Ile Ile Cys Pro Thr
            260                 265
```

POLYPEPTIDE CAPABLE OF BINDING TO VASCULAR ENDOTHELIAL GROWTH FACTOR, AND USE THEREOF

CROSS-REFERENCE TO RELATED APPLICATIONS

This application is a U.S. national phase under the provisions of 35 U.S.C. § 371 of International Patent Application No. PCT/KR2015/009710 filed Sep. 16, 2015, which in turn claims priority of Korean Patent Application No. 10-2015-0087476 filed Jun. 19, 2015. The disclosures of such international patent application and Korean priority patent application are hereby incorporated herein by reference in their respective entireties, for all purposes.

TECHNICAL FIELD

The present invention relates to a novel polypeptide capable of binding to vascular endothelial growth factor, and the use thereof, and more particularly to a polypeptide capable of binding to vascular endothelial growth factor to inhibit the activity thereof, a polynucleotide encoding the polypeptide, a vector comprising the polynucleotide, a host cell transformed with the vector, a method of producing the polypeptide by expressing the vector in the host cell, and a composition for preventing or treating age-related macular degeneration or cancer, which comprises the polypeptide.

BACKGROUND ART

Antibody therapeutic agents show less side effects and high treatment efficacy together in the treatment of various diseases compared to chemical agents, and thus global pharmaceutical companies and bioengineering companies intensively invest on the development thereof. At present, a large number of antibody therapeutic agents are used in clinical applications, and many therapeutic agent candidates are under clinical trials.

However, despite such advantages, the antibody therapeutic agents have problems in that production cost is high, it is difficult to escape the existing patent barriers, it is difficult to penetrate into cells due to their large molecular weight, and therapeutic effects of patients are not actually high as expected. Accordingly, in recent years, the development of therapeutic agents based on small-sized non-antibody protein scaffold for replacing the antibody therapeutic agents has been actively conducted. Many studies have revealed that such small-sized non-antibody protein scaffolds have an advantage over the antibody therapeutic agents in that they penetrate cancer tissue with greatly increased efficiency, suggesting that they can offer improved therapeutic effects.

Under this background, the present inventors successfully developed a repebody which is a non-antibody protein scaffold capable of replacing existing antibodies. It was shown that the repebody has a size equal to about ⅕ of that of the immunoglobulin antibody, is produced in large amounts in E. coli, and shows little or no immunogenicity as a result of animal tests (Korean Patent No. 1,517,196). In addition, it has been demonstrated that the repebody has very high thermal and pH stabilities, and is able to very easily increase its ability to bind to a target molecule up to a picomole level, and has remarkably superior specificity to the target molecule is very high (Korean Patent No. 1,356,075, Korean Patent Laid-Open Publication No. 10-2013-0007380).

Vascular endothelial growth factor (VEGF) is a disease-inducing factor which is overexpressed in various cancer cells, including metastatic colorectal cancer cells, to induce angiogenesis, thereby promoting tumor growth and metastasis. It was reported that VEGF is overexpressed in not only tumors, but also blood vessel-related diseases such as age-related macular degeneration (AMD). As such, VEGF overexpression is related to various diseases, and thus studies on the development of therapeutic agents targeting VEGF have been actively conducted.

At present, protein-based drugs targeting VEGF for treatment of age-related macular degeneration (AMD) include Bevacizumab that is a monoclonal antibody, but it was reported that Bevacizumab has lower binding affinity and therapeutic efficacy than other new monoclonal antibody drugs. To overcome this disadvantage, the development of new therapeutic methods, including use in combination with chemotherapy and the development of new drugs, has been attempted. Other VEGF-targeting drugs include Ranibizumab which is a monoclonal antibody fragment (Fab) derived from Bevacizumab. Ranibizumab has been used as an agent for treating age-related macular degeneration, but was reported to have a side effect and limited therapeutic efficacy. Recently, Aflibercept, which is a recombinant protein composed of the extracellular domains of human VEGF receptors 1 and 2 fused to the Fc portion of the human IgG1 immunoglobulin, has been developed and clinically used. Aflibercept is known to offer improved efficacy toward AMD compared to other protein-based drugs, but has some side effects and very expensive. Therefore, there is an urgent need to develop therapeutic agents targeting VEGF for treatment of AMD with a new concept, which overcome the limitations of existing drugs.

The present inventors have successfully developed a specific protein binder for various disease-related target proteins including VEGF by use of the above-described repebody scaffold, and have verified through a cell-based method that the specific protein binder has biological inhibitory effects (Korean Patent No. 10-1517960). However, studies on the application of the specific protein binder are still in the beginning stage, and thus further studies are actively underway.

Under this background, the present inventors have made extensive efforts to successfully obtain a protein that binds specifically to VEGF, which is an important target protein for treatment of age-related macular degeneration and various cancers, using the above-described repebody scaffold, and as a result, have screened a novel polypeptide having a specific binding affinity for VEGF, based on a random mutation library constructed based on the analysis of the structural characteristic (modularity) and overall structure of the repebody. In addition, the present inventors have screened and produced a polypeptide, which is a novel repebody that binds specifically to VEGF, through a beneficial mutation predicted based on a protein complex structure, and have found that the repebody is capable of binding specifically to VEGF and offers therapeutic efficacy in the choroidal neovascularization (CNV) animal model, thereby completing the present invention.

DISCLOSURE OF INVENTION

Technical Problem

It is an object of the present invention to provide a polypeptide capable of binding specifically to vascular endothelial growth factor (VEGF) to inhibit the activity thereof, a polynucleotide encoding the polypeptide, a vector comprising the polynucleotide, a recombinant microorganism having the vector introduced therein, and a method for producing the polypeptide using the recombinant microorganism.

Another object of the present invention is to provide a composition for preventing and treating age-related macular degeneration, which comprises administering a composition for treating age-related macular degeneration or cancer, which comprises the polypeptide.

Technical Solution

To achieve the above object, the present invention provides a polypeptide selectively bound to vascular endothelial growth factor (VEGF), in which an N-terminal of leucine-rich repeat (LRR) family protein having an alpha-helical capping motif, a modified repeat module of variable lymphocyte receptor (VLR) protein, and a C-terminal of the VLR protein are fused, wherein the amino acid(s) at one or more position(s) selected from the group consisting of positions 44, 47, 49, 50, 69, 71, and 72 in the amino acid sequence represented by SEQ ID NO: 2 is mutated.

The present invention also provides a polynucleotide encoding the polypeptide and a recombinant vector comprising the polynucleotide.

The present invention also provides a recombinant microorganism having introduced therein the polynucleotide or the recombinant vector.

The present invention also provides a method for producing a polypeptide, comprising the steps of: (i) culturing the recombinant microorganism to express the polypeptide; and (ii) recovering the polypeptide from the cultured recombinant microorganism or the culture.

The present invention also provides a composition for preventing or treating age-related macular degeneration, which contains the polypeptide as an active ingredient.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Unless defined otherwise, all the technical and scientific terms used herein have the same meaning as those generally understood by one of ordinary skill in the art to which the invention pertains. Generally, the nomenclature used herein and the experiment methods, which will be described below, are those well known and commonly employed in the art.

As used herein, the term "vascular endothelial growth factor" refers to a signaling protein known to be involved in the growth, proliferation and migration of endothelial cells to thereby play an essential role in increased angiogenesis and vascular permeability. Overexpression of VEGF in cells induces excessive angiogenesis and increased vascular permeability, which are found in vascular diseases and various cancers, including age-related macular degeneration, colorectal cancer, breast cancer, and lung cancer.

Figure 1:
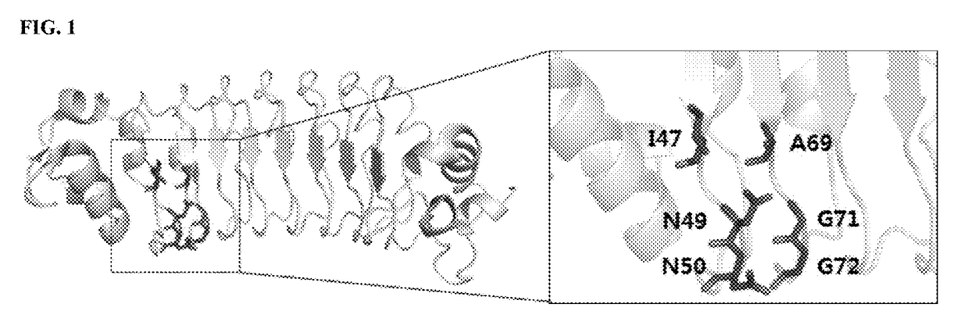
FIG. 1 is a schematic view showing the overall structure of repebody, which indicates amino acid residues in a random library constructed in order to select polypeptides that bind specifically to VEGF.

The present inventors have constructed a library randomly comprising a repeat module of the polypeptide in which an N-terminal of leucine-rich repeat (LRR) family protein having an alpha-helical capping motif, a consensus-designed repeat module of LRR (Leucine-rich repeat) family proteins, and a C-terminal of the VLR (variable lymphocyte receptor) protein are fused, in order to develop a novel polypeptide (repebody) capable of being selectively bound to vascular endothelial growth factor (VEGF), and effectively immobilizing or purifying VEGF (FIG. 1). The polypeptide included in the library may be encoded by a polynucleotide sequence of SEQ ID NO: 1 or a polynucleotide sequence having a homology of 75%, preferably 85%, more preferably 90%, further preferably 95% or more, with the polynucleotide sequence of SEQ ID NO: 1.

In addition, the library may be constructed as a form of phagemid including the polynucleotide. In the present invention, the term "phagemid" means a circular polynucleotide molecule derived from a phage which is a virus having E. coli as a host and includes sequences of proteins and surface-proteins required for propagation and proliferation. A recombinant phagemid may be produced using gene recombinant technology well known in the art, and site-specific DNA cleavage and connection may be performed by an enzyme, generally known in the art, and the like. The phagemid may include a signal sequence or leader sequence for secretion in addition to expression regulating factors such as a promoter, an operator, an initiation codon, a termination codon, an enhancer and may be mainly used in a method for labeling the protein on a surface of the phage by fusing a desired protein with a surface protein of the phage. The promoter of the phagemid is mostly inducible and may include a selective marker for selecting a host cell. For an object of the present invention, the phagemid may be a polynucleotide of SEQ ID NO: 2 disclosed in the prior patent (Korean Patent No. 1,356,075) of the present inventors, including MalEss, DsbAss or PelBss which is a signal sequence or a leader sequence for expressing and secreting the polypeptide-encoding polynucleotide constructing the library, and including a histidine-tag for confirming expression of a recombinant protein on a surface of the phage, and a polynucleotide which encodes gp3 domain which is a kind of a surface protein of M13 phage for expression on the surface of the phage, but the present invention is not particularly limited thereto.

Figure 3:
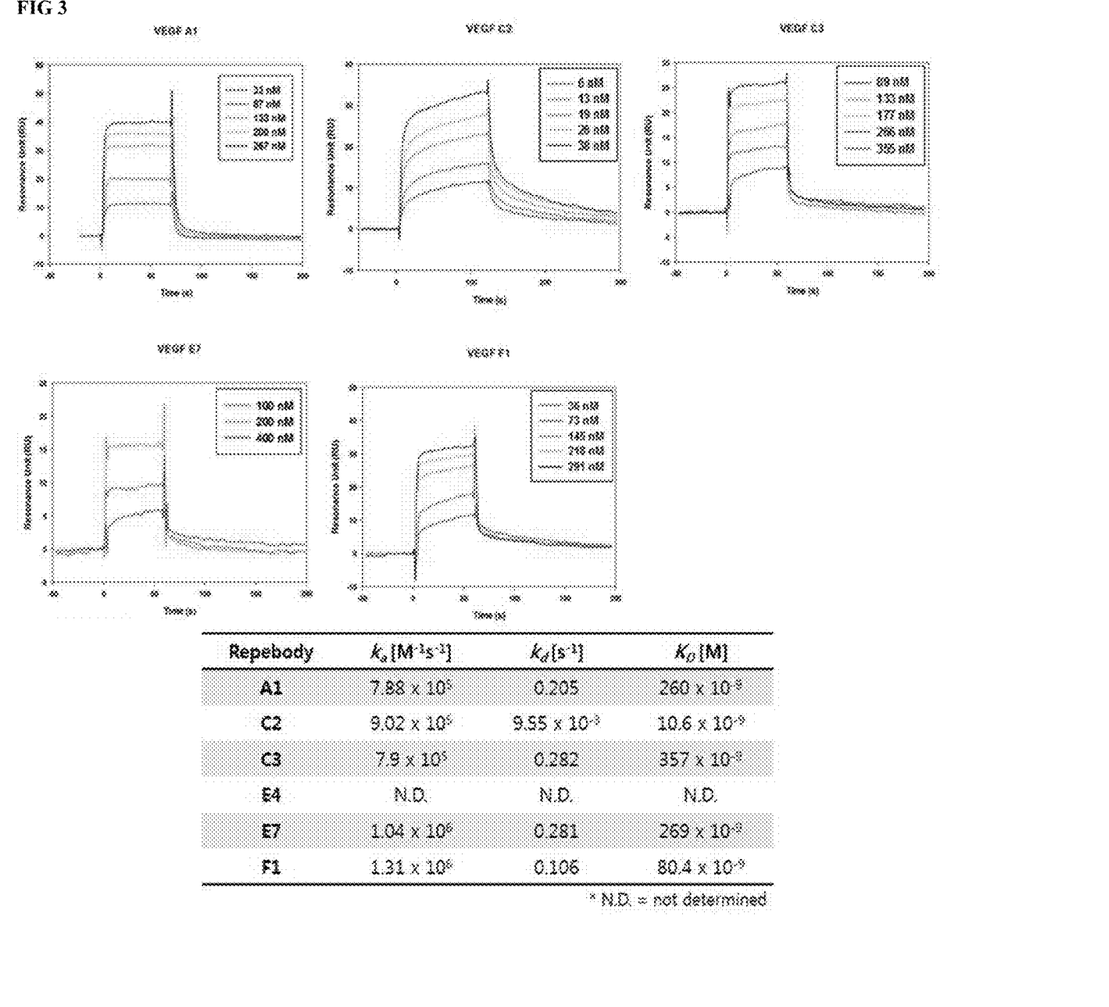
FIG. 3 depicts graphs and a table, which show the results of surface plasmon resonance (SPR) analysis performed to examine the VEGF-binding affinities of the clones having specific binding activities as shown in FIG. 2.
Figure 4:
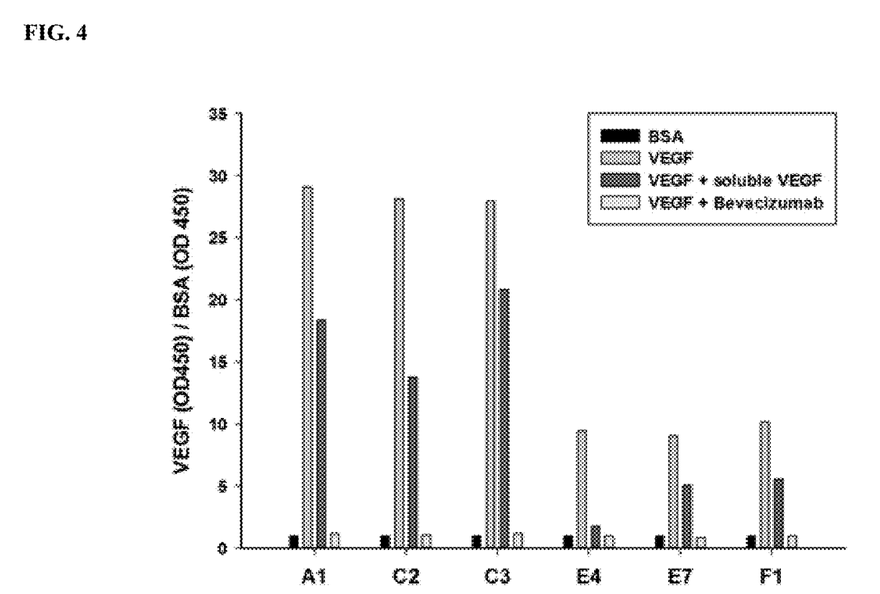
FIG. 4 shows the results of ELISA analysis performed to confirm the specific binding activities of clones to VEGF. It can be seen that all the clones do not bind to BSA, but specifically bind to VEGF. It can be seen that the ELISA signal of VEGF decreased due to the anti-VEGF monoclonal antibody Bevacizumab added as a competitor, suggesting that all the clones recognize an epitope similar to that recognized by Bevacizumab.
Figure 5:
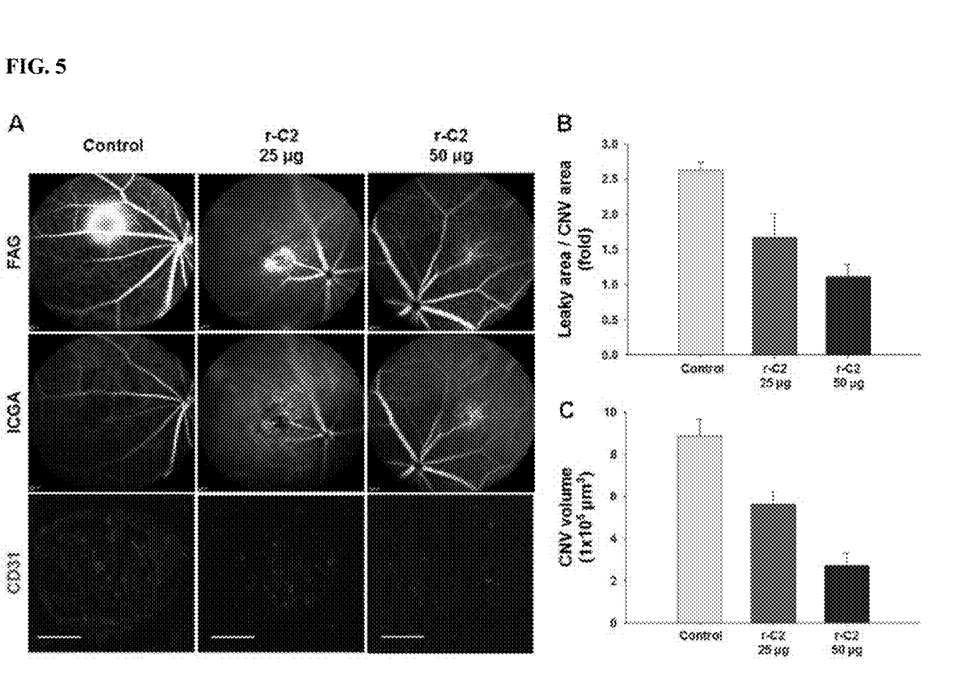
FIG. 5 shows the results of an experiment performed to verify the therapeutic efficacy of the VEGF-binding polypeptide C2 (SEQ ID NO: 4) in macular degeneration mouse models. The two different amounts (25 and 50 µg) of VEGF-binding polypeptide C2 (SEQ ID NO: 4) and a control (PBS) were intravitreally injected into the macular degeneration mouse models, and then difference in neovascularization was compared between the mouse models.

The present inventors selected novel repebody type polypeptides (SEQ ID NOs: 3 to 8) having excellent binding affinity for VEGF by use of a phage display method based on a library including the phagemid, wherein the amino acid(s) at one or two or more position(s) selected from the group consisting of positions 47, 49, 50, 69, 71, and 72 in the amino acid sequence represented by SEQ ID NO: 2 (FIG. 2) is mutated. Furthermore, the present inventors measured the binding affinities of the selected polypeptides (FIG. 3), and found that the polypeptides bind specifically to vascular endothelial growth factor (FIG. 4).

Therefore, in one aspect, the present invention is directed to a polypeptide selectively bound to vascular endothelial growth factor (VEGF), in which an N-terminal of leucine-rich repeat (LRR) family protein having an alpha-helical capping motif, a consensus designed repeat module of LRR (Leucine-rich repeat) family proteins, and a C-terminal of the VLR (variable lymphocyte receptor) protein are fused, wherein the amino acid(s) at one or more position(s) selected from the group consisting of positions 44, 47, 49, 50, 69, 71 and 72 in the amino acid sequence represented by SEQ ID NO: 2 is mutated.

In the present invention, the N-terminal of Leucine rich repeat (LRR) family protein having an alpha-helical capping motif may be an N-terminal of an internalin protein. The internalin protein may be preferably selected from the group consisting of internalin proteins A, B, C, H and J, and more preferably, internalin protein B may be used.

In the present invention, the term "internalin B protein" refers to a kind of the LRR family protein expressed in a *Listeria* strain, and it is known that the internalin B protein has an N-terminal structure different from that of other LRR family proteins in which other hydrophobic cores are uniformly distributed through the entire molecule to thereby be stably expressed even in microorganisms. It is considered that since the N-terminal of the internalin protein which is the most important in folding a repeat module is derived from a microorganism and has a more stable structure including an alpha-helix, such that the internalin protein can be effectively used for stable expression of LRR family proteins in the microorganisms.

In the present invention, the term "N-terminal of an (or the) internalin protein" of the present invention refers to an N-terminal of the internalin protein required for soluble expression and folding of the protein, and means a repeat module of the alpha-helix capping motif and the internalin protein. The N-terminal of the internalin protein may limitlessly include any N-terminal of the internalin protein required for soluble expression and folding of the protein, and as an example thereof, an alpha-helix capping motif "ETITVSTPIKQIFPDDAFAETIKANLKKKSVT-DAVTQNE" and the repeat module may be included. The repeat module pattern may be "LxxLxxLxLxxN". In the repeat module pattern, L means alanine, glycine, phenylalanine, tyrosine, leucine, isoleucine, valine, or tryptophan; N means asparagine, glutamine, serine, cysteine or threonine; and x means any hydrophilic amino acid. In addition, the N-terminal of the internalin protein of the present invention may be selected and used as long as the N-terminal has a high structural similarity depending on a kind of the LRR family protein that can be fused, and the most stable amino acid may be selected by calculation of a binding energy, and the like, and the amino acid of the module corresponding thereto may be mutated.

In the present invention, the term "variable Lymphocyte Receptor (VLR)" refers to a kind of the LRR family protein that is expressed and performs an immune function in hagfishes and lampreys, and is usefully used as a backbone capable of binding to various antigenic substances. A polypeptide in which the N-terminal of the internalin B protein and the VLR protein are fused is relatively increased in solubility and expression amount as compared to a VLR Protein that is not fused with the internalin B protein, and thus the polypeptide can be used in the preparation of a novel protein therapeutic agent based on the increase of solubility and expression amount.

In the present invention, the term "variable Lymphocyte Receptor (VLR)" refers to a kind of the LRR family protein that is expressed and performs an immune function in hagfishes and lampreys, and is usefully used as a backbone capable of binding to various antigenic substances. A polypeptide in which the N-terminal of the internalin B protein, the consensus-designed repeat module of LRR family proteins, and a C-terminal of the VLR (variable lymphocyte receptor) protein are fused is relatively increased in solubility and expression amount as compared to a VLR Protein that is not fused with the internalin B protein, and thus the polypeptide can be used in the preparation of a novel protein therapeutic agent based on the increase of solubility and expression amount.

In the present invention, the term "repebody" is a polypeptide optimized by consensus design through fusion of the N-terminal of the internalin B having the LRR protein structure and the VLR based on the structural similarity. The repebody protein may be structurally divided into a concave region and a convex region. Here, it is known that the concave region has high variety of the sequence and is important in protein interaction. On the contrary, the convex region serves to stably maintain the entire structure of protein based on the highly conserved sequence. The repebody protein may include all fusion LRR family protein obtained by using all proteins included in the LRR family having the repeat module to improve the solubility expression and biophysical properties of protein of all protein by the above-described method.

In the present invention, the polypeptide may comprise an amino acid sequence represented by any one of SEQ ID NOs: 3 to 8.

In the present invention, the polypeptide may bind to vascular endothelial growth factor (VEGF) to inhibit the activity of the vascular endothelial growth factor.

In another aspect, the present invention is directed to a polynucleotide that encodes the polypeptide.

In the present invention, the polynucleotide may be a polynucleotide encoding any one amino acid sequence of SEQ ID NOs: 3 to 8, and may be a polynucleotide having a base sequence having a homology of 70% or more, more preferably 80% or more, and more preferably 90% or more, with the polynucleotide, but is not particularly limited thereto.

In still another aspect, the present invention is directed to a vector comprising the polynucleotide.

As used herein, the term "vector" may be a DNA product containing base sequence of polynucleotide encoding a target protein operably linked to an appropriate regulation sequence so as to express the target protein in a suitable host cell. The regulation sequence may include a promoter capable of initiating transcription, any operator sequence for regulating such transcription, a sequence encoding an appropriate mRNA ribosome binding site, and a sequence regulating termination of transcription and decoding. The vector may be transformed or transfected into a suitable host and then may be replicated or may perform functions regardless of the host genome, and may be integrated into a genome itself.

The vector used in the present invention is not particularly limited as long as it is capable of being replicated in host cells, and may be any vector known in the art. Examples of the vector that is generally used may include plasmid, phagemid, cosmid, virus, and bacteriophage in a natural state or in a recombinant state. For example, as the phage vector or the cosmid vector, pWE15, M13, λMBL3, µMBL4, λIXII, λASHII, λAPII, λt10λt11, Charon4A, and Charon21A, etc., may be used, and as the plasmid vector, pBR-based, pUC-based, pBluescriptII-based, pGEM-based, pTZ-based, pCL-based and pET-based, etc., may be used. The vector usable in the present invention is not particularly limited, but may be any known expression vector. Preferably, pACYC177, pACYC184, pCL, pECCG117, pUC19, pBR322, pMW118, pCC1BAC, pET-21a, pET-32a vectors, etc., may be used. Most preferably, the pET-21a vector and the pET-32a vector may be used.

In yet another aspect, the present invention is directed to a recombinant microorganism having introduced therein the polynucleotide or the vector comprising the polynucleotide.

In the present invention, the term "recombinant microorganism" means a transfected cell in which a vector having a gene encoding one or more target proteins is introduced into a host cell to express the target protein, and may include all cells such as eukaryotic cells, prokaryotic cells, and the like. Examples thereof may include bacteria cells such as *E. coli, Streptomyces, Salmonella typhimurium*, and the like; yeast cells; fungus cells such as *pichiapastoris*, and the like; insect cells such as *Drosophila, spodoptera* Sf9 cell, and the like; animal cells such as CHO, COS, NSO, 293, bow melanoma cell; or plant cells, but the present invention is not particularly limited thereto. A host cell that may be used in the present invention is not particularly limited, but *E. coli* may preferably be used as a host cell. Most preferably, *E. coli* BL21 (DE3) or OrigamiB (DE3) may be used as a host cell.

As used herein, the term "transfection" means that a vector containing polynucleotide encoding a target protein is introduced into a host cell so that the protein encoded by the polynucleotide is capable of being expressed in the host cell. The transfected polynucleotide may be any one regardless of the position as long as the polynucleotide is capable of being expressed in the host cell, regardless of the matter that the polynucleotide is inserted and positioned into chromosome of the host cell or positioned on an outer portion of the chromosome. In addition, the polynucleotide includes DNA and RNA encoding the target protein. The polynucleotide may be inserted with any type as long as the polynucleotide is capable of being introduced into the host cell to be expressed. For example, the polynucleotide may be introduced into the host cell as an expression cassette form which is a gene structure, including all factors required for self expression. The expression cassette may include a promoter which is operably linked to the polynucleotide, a transcription termination signal, a ribosome binding site, and a translation termination signal. The expression cassette may be in the form of a self-replicable expression vector. In addition, the polynucleotide may be introduced into the host cell as itself to be operably linked to the sequence required for expression in the host cell.

In a further aspect, the present invention is directed to a method for producing a polypeptide, comprising the steps of: (i) culturing the recombinant microorganism to express the polypeptide; and (ii) recovering the polypeptide from the cultured recombinant microorganism or the culture.

In the present invention, the culturing of the recombinant microorganism may be preferably performed by a batch culture method, a continuous culture method, a fed-batch culture, and the like, known in the art, but the present invention not particularly limited thereto, wherein culture conditions are not particularly limited, but specifically, pH may be appropriately adjusted (pH 5 to 9, preferably pH 6 to 8, most preferably pH 6.8) by using a basic compound (for example: sodium hydroxide, potassium hydroxide or ammonia) or an acidic compound (for example, phosphoric acid or sulfuric acid), and an aerobic condition may be maintained by introducing oxygen, or an oxygen-containing gas mixture into the culture, and the culturing may be performed at a culture temperature of 20 to 45° C., preferably, 25 to 40° C. for about 10 to 160 hours. The polypeptide produced by the culture may be secreted into the medium or remained in the cell.

In addition, in the culture medium to be used, as carbon source, sugar and carbohydrate (for example, glucose, sucrose, lactose, fructose, maltose, molasse, starch and cellulose), oil and fat (for example, soybean oil, sunflower seed oil, peanut oil and coconut oil), fatty acid (for example, palmitic acid, stearic acid and linoleic acid), alcohol (for example, glycerol and ethanol) and organic acid (for example, acetic acid), and the like, may be used individually or by mixing. As nitrogen source, nitrogen-containing organic compound (for example, peptone, yeast extract, gravy, malt extract, corn steep liquor, soybean meal powder and urea), or inorganic compound (for example, ammonium sulfate, ammonium chloride, ammonium phosphate, ammonium carbonate and ammonium nitrate) and the like, may be used individually or by mixing. As phosphate source, potassium dihydrogen phosphate, dipotassium hydrogen phosphate, sodium-containing salt corresponding thereto, and the like, may be used individually or by mixing. The culture medium may also include essential growth-promoting materials such as other metal salts (for example, magnesium sulfate or iron sulfate), amino acids and vitamins.

In the recovering of the polypeptide produced in the culturing of the present invention, the desired polypeptide may be recovered from a culture solution using appropriate methods known in the art according to a culture method, for example, a batch culture method, a continuous culture method, a fed-batch culture, or the like.

In a still further aspect, the present invention is directed to a composition for preventing or treating cancer, which comprises the polypeptide.

In a yet further aspect, the present invention is directed to a composition for preventing and treating age-related macular degeneration, which comprises the polypeptide.

In the present invention, the prevention or treatment of cancer may be achieved by the binding of the polypeptide to vascular endothelial growth factor.

In the present invention, the prevention or treatment of age-related macular degeneration may be achieved by the binding of the polypeptide to vascular endothelial growth factor.

As used herein, the term "cancer" or "tumor" refers to a mass caused by the abnormal growth of body tissue. Because vascular endothelial growth factor (VEGF) is a growth factor that induces tumor proliferation and angiogenesis, the term "cancer" or "tumor" as used herein is meant to include all of colorectal carcinoma, colorectal cancer, non-small-cell lung cancer, ovarian cancer, multiple myeloma, Castleman's disease, liver cancer and the like, which secrete an excessive amount of vascular endothelial growth factor.

As used herein, the term "age-related macular degeneration" means a disease in which degeneration of macula occurs to cause visual impairment, in which the macula is a nerve tissue which is located in the central portion of the eye's inner retina and in which most of photoreceptor cells are gathered and the object's image is formed. Vascular endothelial growth factor (VEGF) is a growth factor that induces angiogenesis in the retina, and thus "age-related macular degeneration" in the present invention is meant to include all types of macular degeneration caused by excessive secretion of vascular endothelial growth factor.

As used herein, the term "treating" refers to not only inhibiting or alleviating one or more symptoms caused by age-related macular degeneration or cancer, but also treating cancer or preventing the progression of age-related macular degeneration or cancer, by administering the composition. As used herein, the term "preventing" refers to all actions that inhibit age-related macular degeneration or cancer or delay the onset of age-related macular degeneration or cancer by administering the composition. In the present invention, the treatment of age-related macular degeneration or cancer is achieved by the binding of the polypeptide of the present invention to vascular endothelial growth factor. Specifically, age-related macular degeneration is treated by allowing the polypeptide to bind to the vascular endothelial growth factor to significantly inhibit the activity of the vascular endothelial growth factor.

A prior patent (Korean Patent No. 1,517,196) to the present invention discloses that a novel repebody capable of binding interleukin-6 has a significant anticancer effect against non-small lung cancer. Thus, it is evident that a repebody of the present invention, which binds specifically to vascular endothelial growth factor, may also be used for the prevention or treatment of cancer caused by overexpression of vascular endothelial growth factor.

However, whether repebody is effective as an agent for treating age-related macular degeneration is not yet known. Accordingly, the present inventors constructed macular degeneration mouse models, namely CNV (choroidal neovascularization) mouse models, by a laser photocoagulation method in order to evaluate the therapeutic efficacy of the repebody according to the present invention. When the mice were treated with polypeptide C2 of SEQ ID NO: 4 by intraocular injection, choroidal neovascularization significantly decreased, indicating that the repebody is effective as an agent for treating macular degeneration (FIG. 6).

A composition for treating age-related macular degeneration or cancer, which comprises the polypeptide of the present invention, may further comprise a pharmaceutically acceptable carrier and may be formulated with a carrier.

As used herein, the term "pharmaceutically acceptable carrier" refers to a carrier or diluent that does not impair the biological activity and characteristics of an administered compound without irritating an organism. As a pharmaceutically acceptable carrier in a composition that is formulated as a liquid solution, a sterile and biocompatible carrier is used. The pharmaceutically acceptable carrier may be physiological saline, sterile water, Ringer's solution, buffered saline, albumin injection solution, dextrose solution, maltodextrin solution, glycerol, ethanol, or a mixture of two or more thereof. In addition, the composition of the present invention may, if necessary, comprise other conventional additives, including antioxidants, buffers, and bacteriostatic agents. Further, the composition of the present invention may be formulated as injectable forms such as aqueous solutions, suspensions or emulsions with the aid of diluents, dispersants, surfactants, binders and lubricants.

A composition for preventing or treating age-related macular degeneration or cancer, which comprises the polypeptide of the present invention and the pharmaceutically acceptable carrier, can be applied as any formulation comprising it as an active ingredient and may be prepared as an oral or parenteral formulation. Pharmaceutical formulations of the present invention include those suitable for oral, rectal, nasal, topical (including buccal and sublingual), vaginal or parenteral (including intramuscular, subcutaneous and intravenous) administration or a form suitable for administration by inhalation or insufflation.

Parenteral formulations comprising the composition of the present invention as an active ingredient include injectable forms for subcutaneous, intravenous or intramuscular injection, suppositories, or sprays inhalable via the respiratory organ, such as aerosols. Injectable formulations may be prepared by mixing the composition of the present invention with a stabilizer or a buffer in water to prepare a solution or a suspension, and loading the solution or suspension into ampules or vials to prepare unit dosage forms. Suppository formulations include suppositories or retention enemas, e.g. containing conventional suppository bases such as cocoa buffer or other glycerides. For spray formulations, such as aerosols, a propellant for spraying a water-dispersed concentrate or wet powder may be used in combination with an additive.

In a further aspect, the present invention is directed to a method for preventing or treating age-related macular degeneration or cancer, the method comprising administering the composition for preventing or treating age-related macular degeneration or cancer, which comprises the polypeptide.

As used herein, the term "administration" means introducing a desired material into a patient by any suitable method. The composition of the present invention may be administered through various routes such as an oral or parenteral route, as long as it can reach a desired tissue. For example, the composition of the present invention may be administered in a conventional manner via an oral, rectal, topical, intravenous, intraperitoneal, intramuscular, intra-arterial, transdermal, intranasal, inhalation, intraocular or intradermal route.

The treatment method of the present invention includes administering the composition for preventing or treating cancer or age-related macular degeneration of the present invention in a therapeutically effective amount. It is apparent to those skilled in the art that the suitable total daily dose of the composition can be determined by an attending physician or veterinarian within the scope of sound medical judgment. The specific therapeutically effective amount for any particular patient will depend upon various factors including the type and extent of response to be achieved, specific compositions according to whether other agents are used therewith or not, the patient's age, body weight, health condition, sex and diet, the time and route of administration, the secretion rate of the composition, the duration of treatment, other drugs used in combination or coincident with the composition, and other similar factors well-known in the medical field. Thus, the therapeutically effective amount of the composition for preventing or treating age-related macular degeneration or cancer, which is suitable for the purpose of the present invention, is preferably determined by taking into consideration the above-described factors.

In addition, the inventive method for treating age-related macular degeneration or cancer may be applied to any animal in which the excessive secretion of vascular endothelial growth factor may cause diseases including tumor development and angiogenesis. Examples of animals to which the inventive method may be applied include humans and primate mammals, as well as livestock animals such as cows, pigs, sheep, horses, dogs and cats.

EXAMPLES

Hereinafter, the present invention will be described in further detail with reference to examples. It will be obvious to a person having ordinary skill in the art that these examples are for illustrative purposes only and are not to be construed to limit or change the scope of the present invention. In addition, it will be apparent to those skilled in that art that various modifications and variations can be made without departing from the technical scope of the present invention based on this illustration.

Example 1: Construction of Repebody Library Based on Protein Structure

Repebody consists of continuously connected repeat units having a conserved leucine-repeat sequence, similar to LRR proteins present in nature. The repebody has a modularity maintaining the overall protein structure and a structural characteristic in that it is divided into a concave region and a convex region due to the shape curvature of the overall structure. A hypervariable region like a complementarity determining region (CDR) is positioned in the concave region to mediate a protein-protein interaction. In addition, the convex region plays an important role in maintaining the overall structure of a repebody based on the well conserved LRR sequence. The protein structure of the repebody was analyzed and a random library was designed in the following manner.

Specifically, six amino acid residues 47, 49, 50, 69, 71 and 72 positioned in the concave region of two continuous modules (LRR1 and LRRV1 modules) positioned at the amino terminus were selected, thereby constructing a random mutagenic library based on the amino acid sequence of SEQ ID NO: 2 (FIG. 1).

Then, the selected amino acids were substituted with NKK degenerate codon, thereby synthesizing mutagenic primers for constructing a library.

Next, overlap PCR was performed on two modules using the primers to obtain a library DNA. The library DNA was inserted into the phagemid pBEL118M of SEQ ID NO: 2 (described in a previous patent application filed by the present inventors: (Korean Patent No. 1,356,075)) to obtain a final library phagemid.

The obtained library was introduced into E. coli XL1-Blue by electroporation to obtain a transformant, thereby constructing a library having a diversity of $1.0 \times 10^8$.

Example 2: Selection of Polypeptides, Which Bind Specifically to VEGF, by Use of Random Phage Library

Example 2-1: Selection of Polypeptides, which Bind to VEGF, Through Panning of Repebody Library Using the library constructed in Example 1 above, polypeptides capable of binding to VEGF were selected and purified. In order to select candidates capable of binding to VEGF, 100 µg/ml of VEGF was coated on an immune-tube at 4° C. for 12 hours. The coated tube was washed three times with PBS, followed by blocking with a PBS solution (TPBSA) containing 1% BSA and 0.05% Tween 20 at 4° C. for 2 hours. Thereafter, $10^{12}$ cfu/ml of the purified phage was added to the coated tube and was allowed to react at room temperature for 2 hours. After the reaction has been completed, the unbound phages were washed five times with a PBS solution (TPBS) containing 0.05% Tween 20 for a total of 2 minutes, and then washed twice with PBS. Finally, 1 ml of 0.2 M glycine-HCl (pH 2.2) was added to the immune-tube, and allowed to incubate at room temperature for 13 minutes to elute the VEGF-bound phages, displayed on the surface thereof. The eluate was neutralized with 60 µl of 1.0 M Tris-HCl (pH 9.0), and 10 ml of E. coli XL1-Blue ($OD_{600}$=0.5) which is a host cell was added thereto, followed by plating on a 2xYT plate. The bio-panning process composed of a series of processes as described above was repeatedly performed four times. As a result, it was observed that the phage binding specifically to VEGF was enriched through each panning process. This result means that the number of phage-displayed repebody specifically binding to repebody increases.

Figure 2:
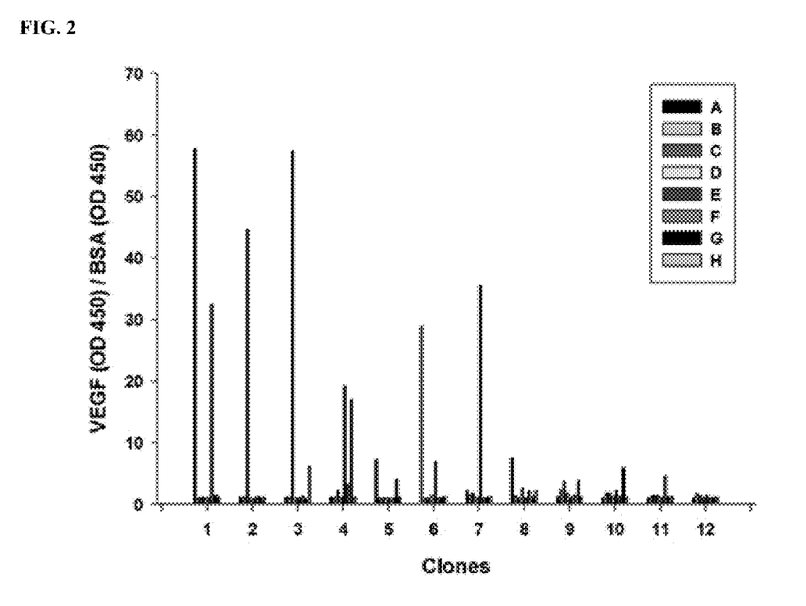
FIG. 2 shows the results of performing phage display biopanning against VEGF by use of a phage library constructed in the present invention. The enzyme-linked immunosorbent assay (ELISA) signals of the binding of clones to VEGF/BSA were normalized, and clones whose signal increased by 10-fold or more were defined as repebody clones having specific binding activity for VEGF.

Example 2-2: Confirmation of Whether the Selected Repebody Binds Specifically to VEGF, and Sequencing of the Selected Repebody The phages selected by the method of Example 2-1 above were subjected to enzyme-linked immunosorbent assay (ELISA) using a 96-well plate coated with VEGF and BSA, thereby selecting 8 repebody candidates in which the absorbance ($OD_{450}$) of VEGF was at least 10 times higher than that of BSA (FIG. 2). The amino acid sequence of each of the candidates was analyzed, and then the clones having the same amino acid sequence were excluded. As a result, a total of six different repebody sequences were found in the selected candidates. The dissociation constants of the six repebodies for VEGF were measured by surface plasmon resonance analysis. As a result, except for the clone E4, the five clones were shown to specifically bind to VEGF (FIG. 3). Especially, it was shown that the amino acid isoleucine at position 47 was substituted with valine, leucine or methionine, and the amino acid asparagine at position 49 was substituted with tyrosine or methionine, the amino acid asparagine at position 50 was substituted with arginine or glutamine, the amino acid alanine at position 69 was substituted with isoleucine or phenylalanine, the amino acid glycine at position 71 was substituted with leucine, isoleucine or phenylalanine, and the amino acid glycine at position 72 was substituted with glutamine, valine or arginine.

Such results suggest that these residues play an important role in allowing repebodies to bind to VEGF.

Example 2-3: Confirmation of Epitope Recognized by the Selected Repebody

It is very important to select a repebody that binds to a portion of VEGF, which interacts with VEGF receptor, from among the VEGF-binding repebodies obtained in Example 2-1 above. Current anti-VEGF monoclonal antibodies bind to the above-described portion to prevent VEGF from interacting with VEGF receptor, thereby effectively inhibiting the activity of VEGF and exhibiting high therapeutic efficacy.

Under this background, using a total of six different repebodies obtained in Example 2-1 above, ELISA was performed. As a result, it was shown that all the six repebodies did not bind to BSA, but had specific binding activity for VEGF (FIG. 4). In addition, when soluble VEGF was added to a plate coated with VEGF, the VEGF signal of ELISA was reduced, indicating that the selected repebodies effectively bind to VEGF even in an aqueous solution state. Finally, competitive ELISA was performed using the anti-VEGF monoclonal antibody Bevacizumab known to bind to a binding interface region of VEGF, which interacts with VEGF receptor. As a result, it was shown that the binding signals of all the repebodies were reduced by Bevacizumab, suggesting that an epitope recognized by the six different repebodies is similar to a binding interface region of VEGF, which interacts with VEGF receptor (FIG. 4).

Example 3: Analysis of the Effect of Polypeptide on Macular Degeneration Mouse Models In order to examine the effect of the polypeptide against choroidal neovascularization (CNV) in macular degeneration, choroidal neovascularization in the eyes of mice was induced by laser photocoagulation, thereby constructing macular degeneration mouse models. Next, each of 25 μg and 50 μg of polypeptide C2 (SEQ ID NO: 4) was injected intravitreally into the mouse models. As a control, PBS was used. At 7 days after injection, mice were anesthetized by intraperitoneal (IP) injection of a mixture of 40 mg/kg of zolazepam/tiletamine (Zoletil; Virbac, Carros Cedex, France) and 5 mg/kg of xylazine (Rompun; Bayer Healthcare, Leverkusen, Germany), followed by pupil dilation with 0.5% tropicamide and 2.5% phenylephrine (Mydrin-P; Santen, Emeryville, Calif.). Fluorescein angiography (FA) and indocyanine green angiography (ICGA) images acquired using a confocal scanning laser ophthalmoscope were analyzed. In this regard, FA detects vascular leaky area caused by retinal and choroidal neovascularization and abnormal neovascularization, and ICGA detects choroidal neovascularization area. The degree of macular degeneration can be measured by the ratio of leaky area measured by FA to CNV area measured by ICGA. As a result, it could be seen that the leaky area/CNV area value significantly decreased in the group treated with C2. In addition, it could be seen that, as the amount of C2 used for treatment increased, the leaky area/CNV area value further decreased (FIG. 6).

In order to measure the CNV volume, the retinal pigment epithelium-choroid complexes of the macular degeneration mouse models were extracted and subjected to immunohistochemistry using an antibody that binds to the vascular endothelial marker CD31. As a result, it could be seen that the CNV volume significantly decreased in the group treated with C2. In addition, it could be seen that, as the amount of C2 used for treatment increased, the CNV volume significantly decreased (FIG. 6).

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

The novel polypeptide of the present invention is capable of binding to vascular endothelial growth factor to inhibit the activity thereof, and thus can be effectively used to develop an agent for preventing or treating various diseases associated with vascular endothelial growth factor (VEGF).

The invention claimed is:

1. A polypeptide capable of binding to vascular endothelial growth factor (VEGF) comprising the amino acid sequence of any one of SEQ ID NOs: 3 to 8.

2. The polypeptide of claim 1, wherein the polypeptide inhibits the activity of VEGF upon binding thereof.

3. A composition for treating age-related macular degeneration, comprising the polypeptide of claim 1 and a pharmaceutically acceptable carrier.

* * * * *

UNITED STATES PATENT AND TRADEMARK OFFICE
CERTIFICATE OF CORRECTION

PATENT NO. : 10,508,138 B2
APPLICATION NO. : 15/737937
DATED : December 17, 2019
INVENTOR(S) : Hak-Sung Kim Page 1 of 1

It is certified that error appears in the above-identified patent and that said Letters Patent is hereby corrected as shown below:

In the Specification

Column 9, Line 39: after "the prevention or treatment of", and before "cancer", insert the phrase -- age-related macular degeneration or --.

Signed and Sealed this
Fourth Day of February, 2020

Andrei Iancu
*Director of the United States Patent and Trademark Office*